United States Patent
Kavteladze et al.

(10) Patent No.: US 11,419,715 B2
(45) Date of Patent: Aug. 23, 2022

(54) BIFURCATED STENT GRAFT SYSTEM FOR THE TREATMENT OF THE ABDOMINAL AORTIC ANEURYSM AND A METHOD OF TREATMENT OF THE ABDOMINAL AORTIC ANEURYSM USING THE SYSTEM

(71) Applicants: Zaza Kavteladze, Potomac, MD (US); David Kavteladze, Potomac, MD (US)

(72) Inventors: Zaza Kavteladze, Potomac, MD (US); David Kavteladze, Potomac, MD (US)

(*) Notice: Subject to any disclaimer, the term of this patent is extended or adjusted under 35 U.S.C. 154(b) by 0 days.

(21) Appl. No.: 17/115,884

(22) Filed: Dec. 9, 2020

(65) Prior Publication Data
US 2021/0275288 A1    Sep. 9, 2021

(30) Foreign Application Priority Data
Mar. 4, 2020 (RU) .............................. RU2020109501

(51) Int. Cl.
*A61F 2/07*   (2013.01)
*A61F 2/852*   (2013.01)
*A61F 2/90*   (2013.01)
*A61F 2/06*   (2013.01)
*A61B 17/06*   (2006.01)

(52) U.S. Cl.
CPC .......... *A61F 2/07* (2013.01); *A61F 2002/065* (2013.01); *A61F 2002/077* (2013.01); *A61F 2220/0016* (2013.01); *A61F 2230/0091* (2013.01)

(58) Field of Classification Search
None
See application file for complete search history.

(56) References Cited

U.S. PATENT DOCUMENTS

| | | | |
|---|---|---|---|
| 6,682,537 B2* | 1/2004 | Ouriel | A61B 17/221 600/585 |
| 6,942,691 B1* | 9/2005 | Chuter | A61F 2/07 623/1.35 |
| 2002/0123790 A1* | 9/2002 | White | A61F 2/07 623/1.36 |

(Continued)

*Primary Examiner* — Ann Schillinger
(74) *Attorney, Agent, or Firm* — Banner & Witcott, Ltd.

(57) ABSTRACT

Devices and associated methods are disclosed for improving the fixation of the stent graft to the wall of the abdominal aortic neck and to increase the tightness of the aneurysmal sac from the main lumen of the abdominal aorta. Particular embodiments are directed to a bifurcated stent graft system for the treatment of the abdominal aortic aneurysm, which includes an aortic bifurcation segment, two iliac segments and an additional inner segment. The aortic bifurcation segment contains a main tubular body with branched legs at the distal end made of biocompatible fabric material attached to and supported by stents. The proximal end of the aortic bifurcation segment is configured to engage with a part of the aorta, without aneurysmal dilatation, proximal to the renal arteries and contains only a metal expandable frame (for example, a stent), without fabric material, but with fixing pins for engagement with the aortic wall proximal to the renal arteries. The part of the aortic bifurcation segment placed in the proximal neck of the abdominal aortic aneurysm is made only of stent/stents, without biocompatible fabric material, but with fixing multidirectional (for example, caudally and cranially) pins on the outer surface for engagement with the aortic wall.

16 Claims, 6 Drawing Sheets

(56) References Cited

U.S. PATENT DOCUMENTS

| | | | |
|---|---|---|---|
| 2003/0125797 A1* | 7/2003 | Chobotov | A61F 2/07 623/1.13 |
| 2003/0176912 A1* | 9/2003 | Chuter | A61F 2/915 623/1.13 |
| 2004/0106978 A1* | 6/2004 | Greenberg | A61F 2/95 623/1.13 |
| 2004/0117003 A1* | 6/2004 | Ouriel | A61F 2/07 623/1.35 |
| 2005/0131516 A1* | 6/2005 | Greenhalgh | A61F 2/07 623/1.13 |
| 2006/0025851 A1* | 2/2006 | Khan | A61F 2/07 623/1.38 |
| 2006/0178733 A1* | 8/2006 | Pinchuk | A61F 2/07 623/1.35 |
| 2007/0173929 A1* | 7/2007 | Boucher | A61F 2/07 623/1.35 |
| 2008/0046065 A1* | 2/2008 | Hartley | A61F 2/07 623/1.13 |
| 2008/0288044 A1* | 11/2008 | Osborne | A61F 2/07 623/1.36 |
| 2009/0099649 A1* | 4/2009 | Chobotov | A61F 2/966 623/1.36 |
| 2009/0248144 A1* | 10/2009 | Bahler | A61F 2/07 623/1.42 |
| 2009/0270967 A1* | 10/2009 | Fleming, III | A61F 2/07 623/1.11 |
| 2011/0071614 A1* | 3/2011 | Majercak | A61F 2/07 623/1.14 |
| 2011/0224774 A1* | 9/2011 | Silveira | A61F 2/07 623/1.2 |
| 2013/0261734 A1* | 10/2013 | Young | A61F 2/07 623/1.22 |
| 2015/0039074 A1* | 2/2015 | Shalev | A61F 2/856 623/1.11 |
| 2015/0374517 A1* | 12/2015 | Majercak | A61F 2/90 623/1.13 |

* cited by examiner

BIFURCATED STENT GRAFT SYSTEM FOR THE TREATMENT OF THE ABDOMINAL AORTIC ANEURYSM AND A METHOD OF TREATMENT OF THE ABDOMINAL AORTIC ANEURYSM USING THE SYSTEM

CROSS-REFERENCE TO RELATED APPLICATIONS

This application claims priority to Russian patent application RU 2020109501, filed Mar. 4, 2020. Benefit of the filing date of this application under 35 U.S.C. § 119 is hereby claimed. This application is hereby incorporated by reference in its entirety.

FIELD OF THE INVENTION

The claimed group of inventions relates to medicine and medical technology, namely to endovascular surgery, and in particular to a stent graft system and a method of treatment of infrarenal aneurysms of the abdominal aorta using the system.

DESCRIPTION OF RELATED ART

An aneurysm is pathological vasodilation resulting from degenerative processes in the artery wall. The larger the diameter of an aneurysm, the greater the rupture rate. Mortality in case of a rupture, despite the great achievements of modern cardiovascular surgery, ranges from 30 to 70%, depending on the localization of the aneurysm: isolated thoracic or abdominal, or thoracoabdominal. In terms of rates, aortic aneurysms are more likely to occur in the abdominal region, usually in the infrarenal region between the renal arteries and the aortoiliac bifurcation.

Currently, the method of endovascular treatment of aortic aneurysms is being actively introduced into clinical practice. This approach was introduced primarily with the aim of reducing trauma and, as a consequence, mortality from open surgical methods of treating this pathology. In fact, it turned out that the endovascular method for the treatment of aortic aneurysms showed a significantly greater safety profile with comparable clinical efficacy in comparison with open surgery (except for cases involving complex anatomy). To a large extent, it became possible due to the development of devices used in the endovascular approach, namely stent grafts. Stent graft is a tube of synthetic or biological material connected to a metal component that provides support. Stent grafts have many requirements mainly related to either the fabric component (permeability, biocompatibility, non-thrombogenicity, flexibility, strength and wear resistance), or to the frame component (developed radial force, radial stiffness, elasticity, radiopacity, corrosion and wear resistance). In addition to the requirements for the components, the design of the stent graft must also solve the problems posed, especially those related to the anatomy of the aorta and its branches. Considering many years of experience in the clinical use of stent grafts in the world, the only significant complications associated with the use of stent grafts are the migration of the stent graft and persistent blood flow in the aneurysmal sac—endoleaks.

The most frequently used in the treatment of infrarenal abdominal aortic aneurysms are modular systems of bifurcated stent grafts (e.g., known from patents U.S. Pat. No. 7,887,576, 9,687,337 or under ZENITH®, Endurant™ trademarks). Known systems usually consist of three modules: a bifurcated main body with suprarenal fixation (aortic bifurcation segment containing a main tubular body with branched legs at the distal end and a stent, without fabric material, but with fixing pins for engagement with the aortic wall proximal to the renal arteries, at the proximal end) and two leg modules (two iliac tubular segments). The main body and leg modules are tubular bodies made of biocompatible fabric material attached to and supported by stents. The main body is located in the aorta. The leg modules are located in the iliac arteries and connect to the main body.

However, over time, as a result of the physiological process of arterial disease and aneurysm growth, both fixation and sealing can be compromised. For example, the aortic neck can expand further due to the progression of atherosclerotic disease or mechanical action of the stent. Thus, the stent graft can lose its seal in relation to the aortic walls, leading to the formation of endoleaks. Naturally, endoleaks can be a serious problem preventing the stent graft from performing its function. An endoleak, even relatively small, can enlarge the aneurysm, increasing the risk of rupture. Impaired seating can also reduce the frictional forces that hold the stent graft in place. In addition, the fixation provided by the pins can be compromised due to the failure of pin fixation or the local rupture of the aortic wall. Loss of fixation is highly undesirable and can also contribute to mortality and morbidity in patients. In addition, migration of the stent graft can result in a type I endoleak and increase the need for surgery to remove the endoleak.

Thus, the main technical problems solved by the implementation and use of the claimed group of inventions, and which could not be solved by the implementation or use of analogues of the invention, are the migration of the stent graft and the persistence/occurrence of blood flow (endoleak) in the aneurysmal sac.

SUMMARY OF THE INVENTION

The technical result provided by the claimed group of inventions when solving the above technical problem is to improve the fixation of the stent graft to the wall of the abdominal aortic neck and to increase the tightness of the aneurysmal sac from the main lumen of the abdominal aorta.

The above problem is solved and the technical result is provided by the proposed bifurcated stent graft system for the treatment of the abdominal aortic aneurysm, which includes an aortic bifurcation segment, two iliac segments and an additional inner segment.

The aortic bifurcation segment contains a main tubular body with branched legs at the distal end made of biocompatible fabric material attached to and supported by stents. The proximal end of the aortic bifurcation segment is configured to engage with a part of the aorta without aneurysmal dilatation, proximal to the renal arteries and contains only a metal expandable frame (for example, a stent), without fabric material, but with fixing pins for engagement with the aortic wall proximal to the renal arteries. The part of the aortic bifurcation segment placed in the proximal neck of the abdominal aortic aneurysm is made only of stent/stents, without biocompatible fabric material, but with fixing multidirectional (for example, caudally and cranially) pins on the outer surface for engagement with the aortic wall.

Each of the iliac segments contains a tubular body made of biocompatible fabric material attached to and supported by stents, while the proximal end of each iliac segment can be connected to the lumen of the leg of the aortic bifurcation segment.

The additional inner segment is made for a tight fit to the part of the aortic bifurcation segment placed in the proximal neck of the abdominal aortic aneurysm and contains a tubular body made of biocompatible fabric material and stents attached to the biocompatible fabric material along the length of the tubular body and supporting it.

To ensure tightness in case of unfavourable anatomy of the proximal aneurysmal neck (for example, short or dilated neck, trapezoidal neck, etc.), the system for treating the abdominal aortic aneurysm may include an additional outer segment containing a body made of biocompatible fabric material. An additional outer segment can be placed around a part of the abdominal aorta below the renal artery branching to ensure tight pressing of the proximal neck of the abdominal aortic aneurysm to the part of the aortic bifurcation segment placed in the proximal neck of the abdominal aortic aneurysm.

An additional outer segment is a belt or ribbon 10 to 30 mm wide forming a circle and equipped with a fastener or buckle or threads for tying a knot.

Also, the above problem is solved, and the technical result is provided by the proposed method of treating the abdominal aortic aneurysm using the previously mentioned system of bifurcated stent graft, which includes the stages at which the aortic bifurcation segment is introduced into the abdominal aorta; the aortic bifurcation segment is placed in contact with the tissues of the aorta so that the metal frame located at its proximal end is connected to the aortic wall proximal to the renal arteries, and part of the aortic bifurcation segment located in the proximal neck of the abdominal aortic aneurysm is connected to the wall of the proximal aneurysmal neck of the abdominal aorta; the first iliac segment is inserted into the left or right iliac artery; the first iliac segment is placed in contact with the tissues of the left or right iliac artery, respectively, and the proximal end of the said iliac segment is connected to the lumen of one of the legs of the aortic bifurcation segment; the second iliac segment is inserted into the other right or left iliac artery; the second iliac segment is placed in contact with the tissues of the other right or left iliac artery, respectively, and the proximal end of the said iliac segment is connected to the lumen of the other leg of the aortic bifurcation segment; a balloon catheter is inserted and additional balloon dilatation of a part of the aortic bifurcation segment located in the proximal neck of the abdominal aortic aneurysm is performed; an additional internal segment is introduced into the aortic bifurcation segment; an additional internal segment is placed in close contact with a part of the aortic bifurcation segment located in the proximal neck of the abdominal aortic aneurysm.

Depending on the medical indication (for large aneurysms), before the introduction of an additional internal segment, a catheter is inserted through the stent cell of a part of the aortic bifurcation segment located in the proximal neck of the abdominal aortic aneurysm into the aneurysmal sac, after which the aneurysmal sac is filled with a thrombotic substance through the catheter, or coils for embolization, and then the catheter is removed.

To ensure tightness in case of unfavourable anatomy of the proximal aneurysmal neck (for example, a short or dilated neck, trapezoidal neck, etc.), after the installation of an additional internal segment, through laparoscopic or open surgical access around the abdominal aorta an additional external segment is introduced below the renal artery branching, containing a body made of biocompatible fabric material, tightened until the walls of the proximal neck of the abdominal aortic aneurysm are tightly pressed against the part of the aortic bifurcation segment located in the proximal neck of the abdominal aortic aneurysm, and fixed on it, while the fixing multidirectional pins on the part of the aortic bifurcation segment located in the proximal neck of the abdominal aortic aneurysm pierce the biocompatible fabric material of the additional outer segment.

BRIEF DESCRIPTION OF THE DRAWINGS

The essence of the proposed group of inventions is reflected in the drawings.

The drawings are not strictly to scale and details that are not necessary for understanding the invention may be omitted. Other elements that are at least substantially equivalent to one another, or have at least substantially equivalent functions to one another are designated by the same number.

Figure 1:
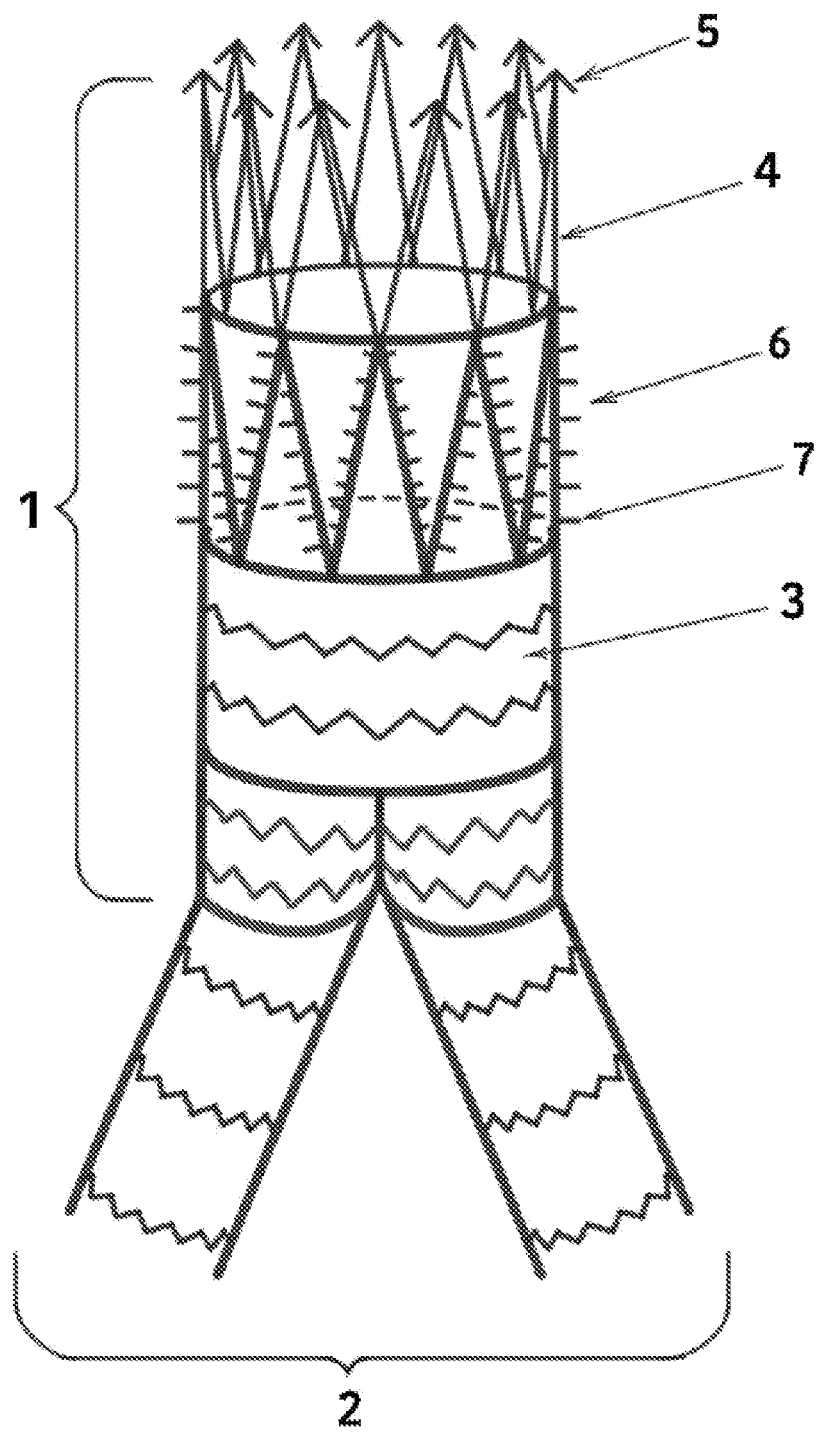
FIG. 1 illustrates the aortic bifurcation segment assembled with iliac segments.
Figure 2:
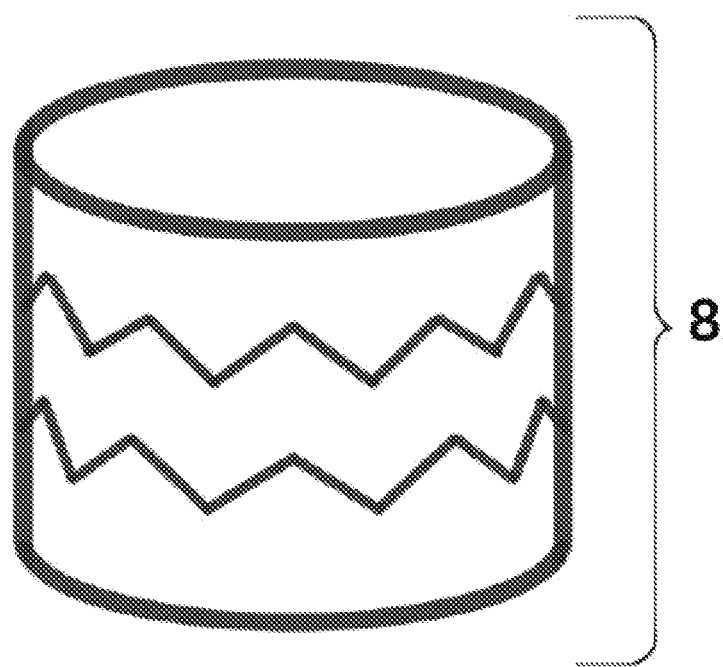
FIG. 2 illustrates an additional segment.

Description of the Links to Parts:
1—aortic bifurcation segment of the bifurcated stent graft system;
2—iliac segments of the bifurcated stent graft system;
3—main body of the aortic bifurcation segment;
4—stent at the proximal end of the aortic bifurcation segment;
5—fixing pins for engagement with the aortic wall proximal to the renal arteries;
6—a part of the aortic bifurcation segment placed in the proximal neck of the abdominal aortic aneurysm made of stent(s) only;
7—fixing multidirectional pins for engaging with the wall of the proximal neck of the abdominal aortic aneurysm;
8—additional internal segment of the bifurcated stent graft system;
9—aneurysmal sac;
10—catheter for filling the aneurysmal sac with a thrombotic substance or coils for embolization;
11—additional outer segment of the bifurcated stent graft system.

DETAILED DESCRIPTION

In the following description, the terms "proximal" and "proximally" are used to indicate position or direction to the patient and/or for insertion into the openings or cavities of the patient's body, and the terms "distal" and "distally" are used to indicate position or direction to or even outside the patient's body. While the description below refers to endovascular grafts (stent grafts) used in the abdominal aorta and iliac arteries to treat the abdominal aortic aneurysm, the use in any other lumens and/or vessels in the body, such as the thoracic aorta and/or branches or peripheral vessels in various modifications is also possible.

The essence of the claimed group of inventions is explained in detail with drawings below.

The proposed bifurcated stent graft system for the treatment of the abdominal aortic aneurysm includes an aortic bifurcation segment (1), two iliac segments (2), and an additional inner segment (8).

In turn, the aortic bifurcation segment contains the main tubular body (3) with branched legs (not indicated in the drawing) at the distal end. The main tubular body of the aortic bifurcation segment is made of biocompatible fabric material (not indicated in the drawing). Examples of biocompatible woven fabrics include polyesters such as polyethylene terephthalate and fluorinated polymers such as polytetrafluoroethylene (PTFE) and foamed PTFE. Examples of biocompatible polyesters include DACRON (DUPONT, Wilmington, Del.) and TWILLWEAVE MICREL (VASCUTEK, Renfrewshire, Scotland). Other examples of biocompatible materials include extracellular matrix (ECM) materials such as purified collagen-based matrix obtained from submucous membranes. The biocompatible fabric material can be one material or can be a mixture, weave, laminate or composite of two or more materials. The biocompatible fabric material may also include other additives such as plasticizers, compatibilizers, surface modifiers, biological materials such as peptides and enzymes, and therapeutic agents such as drugs or other medications.

The biocompatible fabric material is attached to and supported by stents (not indicated in the drawing). For example, standard surgical suturing techniques can be used to attach biocompatible material to stents. Stents can be located both on the inner side of the tubular biocompatible fabric material of the aortic bifurcation segment and on the outer side. Stents can also be squeezed between two layers of biocompatible fabric material, and these stents can also be sutured. Stents can have a wide variety of configurations and can be balloon-expandable or mainly self-expanding. Typically, stents have a circular or cylindrical cross-section when fully expanded to conform to the normally circular cross-section of the body lumen. For example, stents can be discrete stents having a zigzag configuration in which straight bars are set at angles to each other and connected by sharp bends or apexes. Thus, the beams are connected in an endless cycle, forming a mostly tubular structure. Discrete zigzag stents are also called Z-stents. Stents can be made of any rigid biocompatible material such as metal, plastic or ceramic. Preferably, the stents are made of a metal such as stainless steel, nitinol, and other biocompatible alloys. The stents can be equipped with one or more teeth (not shown in the drawing) for attaching the aortic bifurcation segment to the iliac segments of the stent graft. If the stents are anchored to a biocompatible fabric material by suturing, the sutures can be placed along the bars and/or at the bends or tops of the stent.

Figure 3:
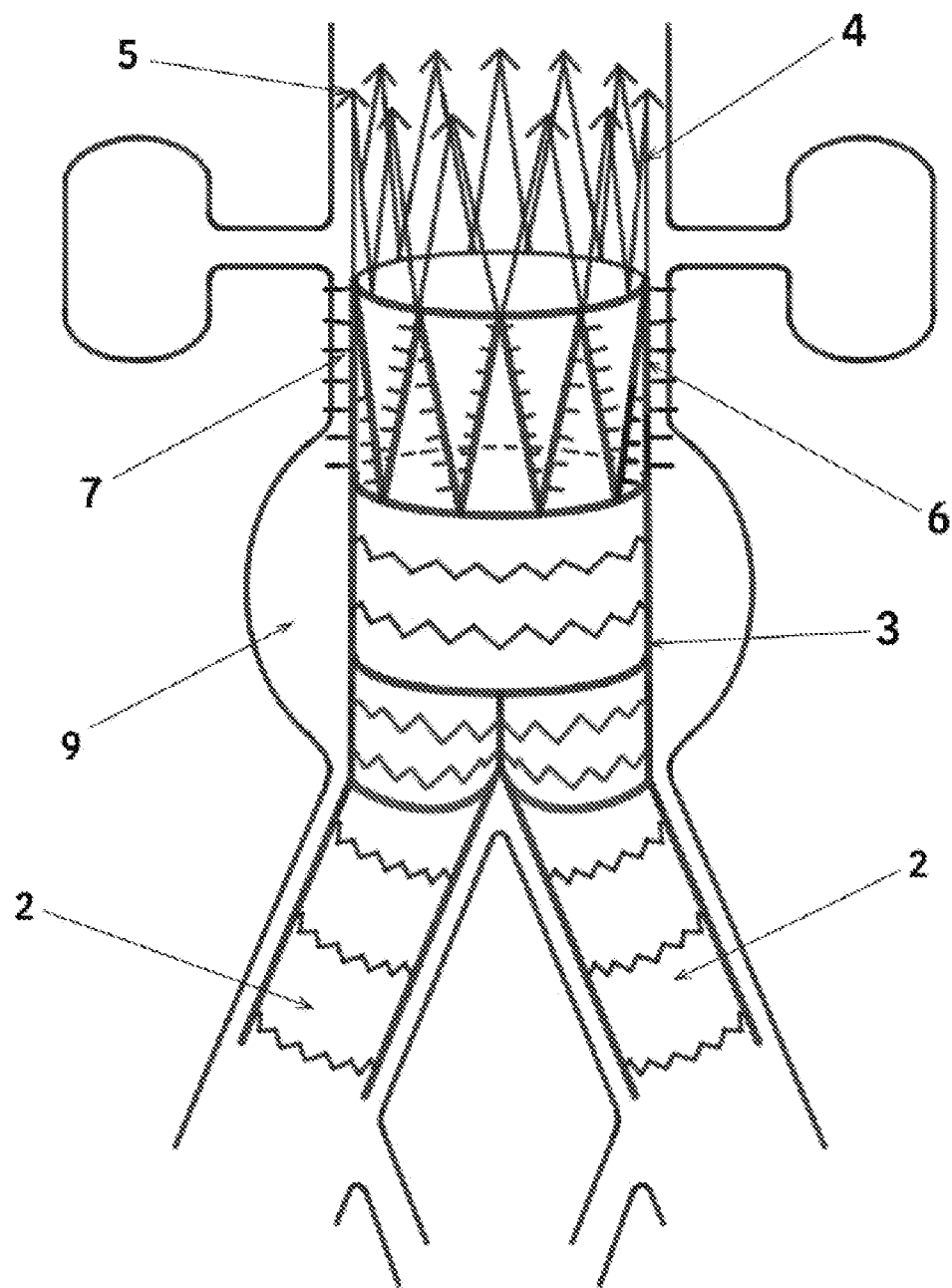
FIG. 3 illustrates the placement of the aortic bifurcation segment and iliac segments in the abdominal aorta and in the iliac arteries, respectively.
Figure 4:
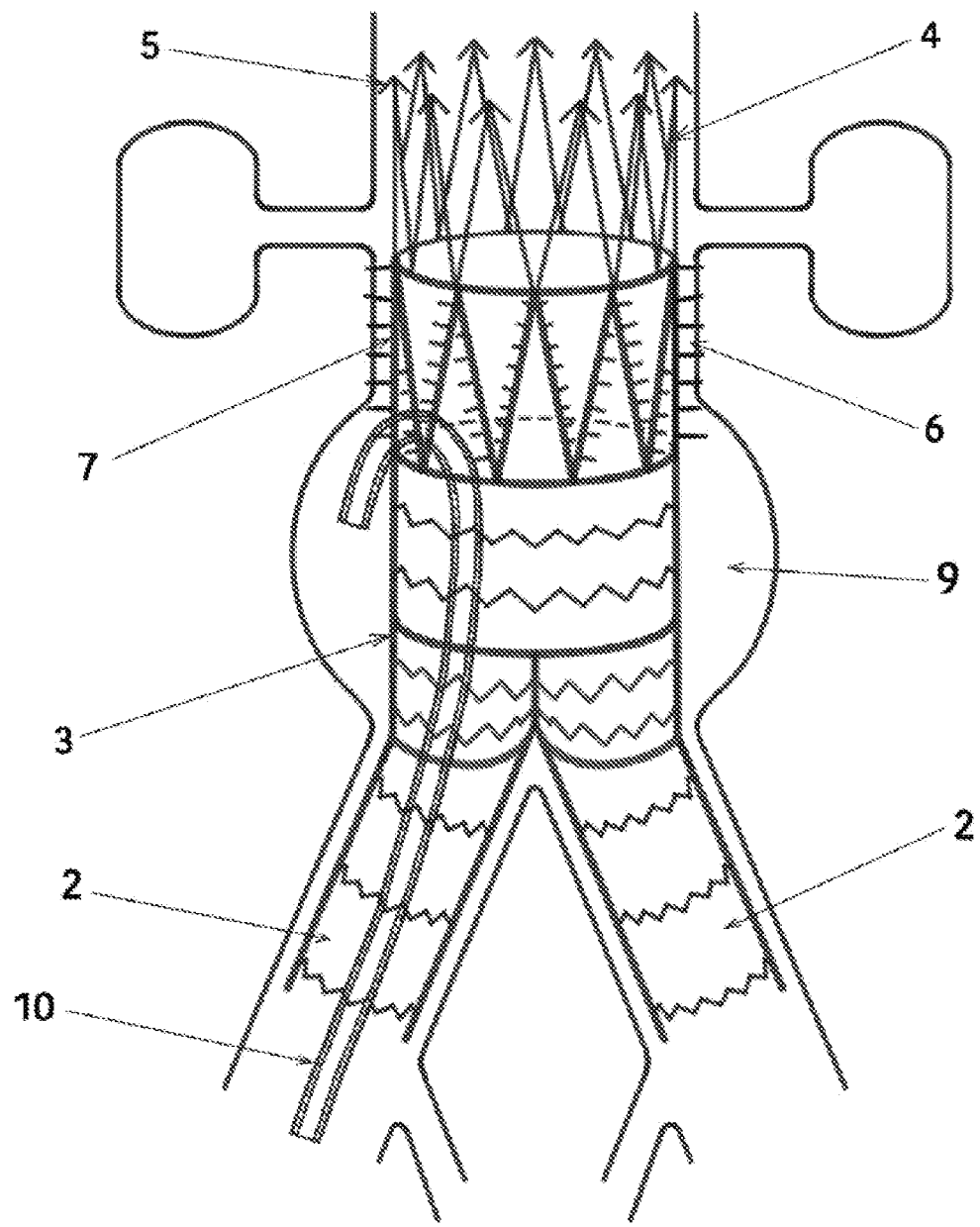
FIG. 4 illustrates the introduction of a catheter into the aneurysmal sac through the stent cell of a part of the aortic bifurcation segment located in the proximal neck of the abdominal aortic aneurysm.
Figure 5:
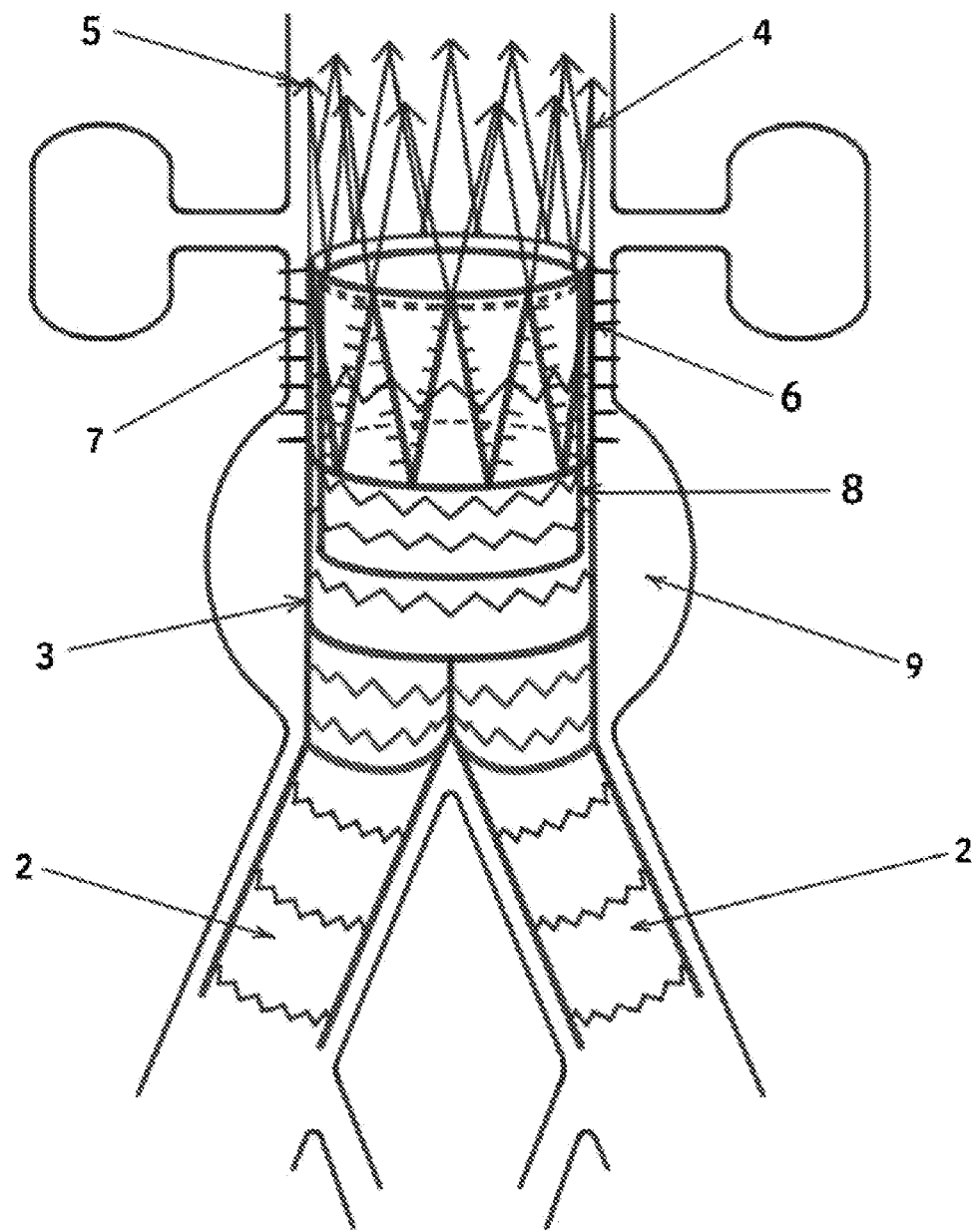
FIG. 5 illustrates an assembled bifurcated stent graft system for treating the abdominal aortic aneurysm.
Figure 6:
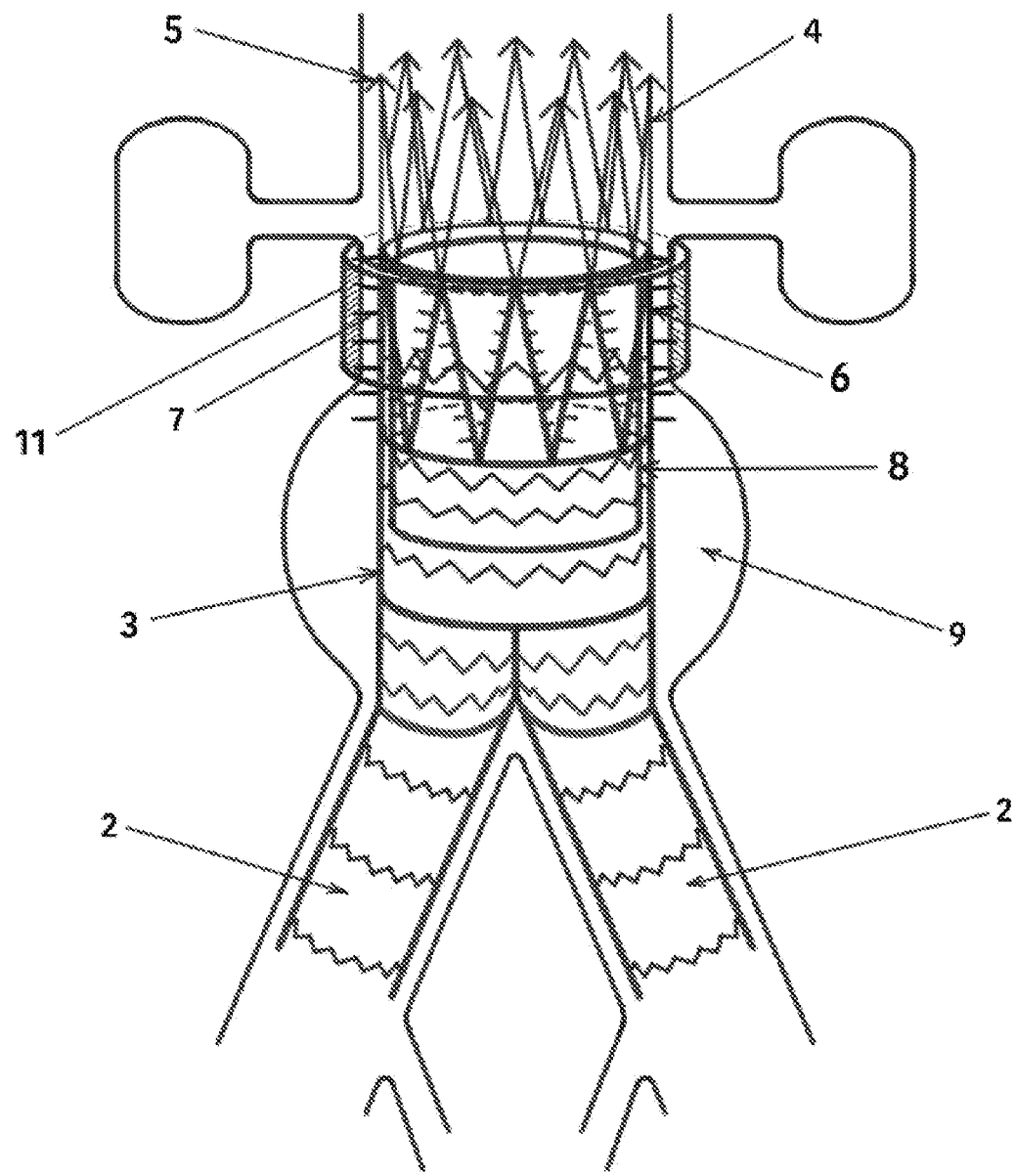
FIG. 6 illustrates the installation of an additional outer segment around the proximal neck of the abdominal aortic aneurysm.

To ensure fixation of the stent graft, the proximal end (4) of the aortic bifurcation segment (1) is configured to engage with the non-aneurysmal part of the aorta without aneurysmal expansion, proximal to the renal arteries (FIG. 3-5). The proximal end of the specified segment contains only an expandable metal frame, for example, a stent (4), without fabric material, but with fixing pins (5) for engaging with the aortic wall proximal to the renal arteries (FIG. 3-5). However, it is also contemplated that other known fixation methods can be used to anchor the stent at a desired location in the vascular system, and more specifically to anchor the proximal end (4) of the aortic stent graft within the aorta.

In addition, to improve fixation, part (6) of the aortic bifurcation segment (1) placed in the proximal neck of the abdominal aortic aneurysm at a distance of 10-20 mm or more is made only of a stent or several stents, without biocompatible fabric material, but with multiple fixing multidirectional (caudal and cranial, or antegrade and retrograde) pins (7) on the outer lateral surface for engagement with the aortic wall. Multiple fixing pins of the part (6) of the aortic bifurcation segment (1) placed in the proximal neck of the abdominal aortic aneurysm pierce the wall of the abdominal aorta, thereby fixing the entire system in relation to the aortic wall with multiple point contacts and simulating not only one circular suture row as in vascular surgery, but a lot. Over time, this only metal part (6) of the aortic bifurcation segment (1) placed in the proximal neck of the abdominal aortic aneurysm has, among other things, the possibility of biological attachment to the aortic wall through full or partial coverage with neointima.

The stent (4) contained at the proximal end of the aortic bifurcation segment, the stent/stents of the part (6) of the aortic bifurcation segment and fixation pins (7) can also be made of the same materials as the stents of the main body (3) of the aortic bifurcation segment (1).

As mentioned earlier, in addition to the aortic bifurcation segment (1), the proposed bifurcated stent graft system also includes two iliac segments (2). Each iliac segment (2) contains a tubular body made of biocompatible fabric material attached to and supported by stents in the same way as the main body (3) of the aortic bifurcation segment (1). The proximal end of each iliac segment (2) is designed to be connected to the lumen of the leg of the aortic bifurcation segment (1), for example, using teeth (not shown in the drawing), which the stents can be equipped with, or a locking mechanism described in U.S. Pat. No. 9,687,337 and incorporated herein by reference.

In addition to the previously mentioned aortic bifurcation segment (1) and two iliac segments (2), the proposed bifurcated stent graft system, in order to increase the tightness and exclude type Ia endoleaks, contains an additional inner segment (8) designed for tight fit from the inside to the part (6) of the aortic bifurcation segment (1) placed in the proximal neck of the abdominal aortic aneurysm (FIG. 3-5) and containing a tubular body made of biocompatible fabric material similar to those used in the aortic bifurcation and iliac segments, and stents attached to the biocompatible fabric material along the length of the tubular body and supporting it. The stents in the accessory segment can also be made of the same materials as the stents of the main aortic bifurcated segment (1) and iliac segments (2).

To ensure tightness in case of unfavourable anatomy of the proximal aneurysmal neck (for example, a short or dilated neck, trapezoidal neck, etc.), the system for treating the abdominal aortic aneurysm may include an additional external segment (11). The additional outer segment (11) contains a body made of biocompatible fabric material similar to the materials used in the aortic bifurcation, iliac and accessory internal segments. An additional outer segment (11) is a belt or ribbon designed to be placed around a part of the abdominal aorta below the renal arteries branching, forming a circle and ensuring tight pressing of the proximal neck of the abdominal aorta to the part of the aortic bifurcation segment placed in the proximal neck of the abdominal aortic aneurysm. A belt or ribbon, depending on the anatomy of the proximal neck of aortic aneurysm, can be 10 to 30 mm wide and is equipped with a fastener or buckle, or threads for tying a knot (not shown in the drawing).

Treatment of the abdominal aortic aneurysm using the above described bifurcated stent graft system is performed as follows:

At the first prehospital stage, to accurately determine the characteristics of the abdominal aortic aneurysm (the size of the aneurysmal sac, the length and diameter of the proximal neck of the aneurysm, the presence of a parietal thrombus), concomitant damage to the great arteries, to determine the possibility of performing endovascular aortic prosthetics and the selection of the necessary stent graft segments, spiral computed tomographic angiography (SCTA) is performed.

Endoprosthetics is performed under subarachnoid anaesthesia using invasive hemodynamic monitoring (measurement of arterial and central venous pressure). If necessary, endarterectomy is performed from the common (CFA), deep and superficial femoral arteries in order to prevent possible ischemia of the lower extremities, plastic surgery of the CFA with autovein or polytetrafluoroethylene material.

Endoprosthetics is performed under subarachnoid anaesthesia using invasive hemodynamic monitoring (measurement of arterial and central venous pressure).

Surgical isolation of the femoral arteries from both sides, imposition of tourniquets.

Catheterization of arteries, placement of wire guides.

Introduction of the aortic bifurcation segment (1) into the abdominal aorta.

Placement of the aortic bifurcation segment (1) in contact with the tissues of the aorta so that the metal frame located at its proximal end, for example, the stent (4), is interlocked with the aortic wall proximal to the renal arteries (FIG. 3), and part of the aortic bifurcation segment placed in the proximal neck of the abdominal aortic aneurysm is interlocked with the wall of the proximal neck of the abdominal aortic aneurysm (FIG. 3). Introduction, positioning and opening the proximal end of the aortic bifurcation segment is a very important moment during which it is necessary to simultaneously securely fix the segment in the aorta both by means of the "crown" (a stent not covered with biocompatible fabric material, placed at the proximal end of the bifurcation segment (4)) and anchoring devices (fixing pins (5), teeth, hooks or spines) and not to compromise the superior mesenteric and renal arteries;

Cannulation of the aortic bifurcation segment (1) with a guide wire on the part of the left or right iliac artery.

Introduction of the first iliac segment (2) into the left or right iliac artery.

Placement (positioning and opening) of the first iliac segment (2) in contact with the tissues of the left or right iliac artery, respectively, and the connection of the proximal end of the specified iliac segment (2) with the lumen of one of the legs of the aortic bifurcation segment (1).

Cannulation of the aortic bifurcation segment (1) with a guide wire on the part of the other left or right iliac artery.

Introduction of the second iliac segment (2) into the other right or left iliac artery.

Placement (introduction, positioning and opening) of the second iliac segment (2) in contact with the tissues of the other right or left iliac artery, respectively, and the connection of the proximal end of the specified iliac segment (2) with the lumen of the other leg of the aortic bifurcation segment (1).

Introduction of a balloon catheter and performing "shrinkage" (additional balloon dilatation) of the proximal, central and distal parts of the bifurcated stent graft system with a balloon catheter, in particular of the part (6) of the aortic bifurcation segment (1) located in the proximal neck of the abdominal aortic aneurysm.

Cannulation of the aortic bifurcation segment (1) from the part of its proximal end (4).

Introduction of an additional internal segment (8) inside the aortic bifurcation segment (1).

Placement (positioning and opening) of the additional internal segment (8) in close contact with the part (6) of aortic bifurcation segment (1) located in the proximal neck of the abdominal aortic aneurysm (FIG. 5). If necessary, for a tighter contact of the additional segment (8) with the part (6) of the aortic bifurcation segment (1) located in the proximal neck of the abdominal aortic aneurysm, it is also possible to perform balloon dilatation of the additional segment (8).

If additional treatment of aneurysm is necessary before the introduction of an additional internal segment, a catheter (10) is inserted into the aneurysmal sac (9) through the stent cell of the part (6) of the aortic bifurcation segment (1) located in the proximal neck of the abdominal aortic aneurysm, after which the aneurysmal sac (9) is filled through the catheter (10) with a thrombotic substance (glue, gel, foam, etc.), or spirals for embolization, and then the catheter is removed (10).

To ensure the tightness of the aneurysmal sac in case of unfavourable anatomy of the proximal aneurysmal neck (short or dilated cervix, trapezoidal neck, etc.), after the installation of the optional inner segment (8), an outer segment (11) containing a body made of biocompatible fabric material, such as a belt or ribbon is introduced after surgical or laparoscopic access around the abdominal aorta below the renal arteries branching. The additional outer segment (11) is tightened until the walls of the proximal neck of the abdominal aortic aneurysm are tightly pressed to the part of the aortic bifurcation segment located in the proximal neck of the abdominal aortic aneurysm, and an additional external segment (11) is fixed on the proximal neck of the abdominal aortic aneurysm by fixing the ends of the mentioned segment with a fastener or buckle (not shown in the drawing) or by connecting them with threads, for example, suture material (not shown in the drawing) and tying the threads. At that, the fixing multidirectional pins (7) on the part (6) of the aortic bifurcation segment located in the proximal neck of the abdominal aortic aneurysm, pierce the biocompatible fabric material of the additional outer segment (11).

In the postoperative period, on the 3-5th day, duplex scanning of the abdominal aorta and great vessels is performed to exclude "leakage" (endoleak) and hemodynamically significant changes in the iliac and femoral arteries. Follow-up MSCT is performed 1, 6, and 12 months after endovascular prosthetics, then once a year.

What is claimed is:

1. A bifurcated stent graft system for the treatment of an abdominal aortic aneurysm, including:

an aortic bifurcation segment comprising a main tubular body that branches, at a distal end thereof, into two tubular legs in fluid communication with the main tubular body, said two tubular legs being made of biocompatible fabric material attached to and supported by stents, wherein a proximal end of the aortic bifurcation segment includes a metal expandable frame, without fabric material, said metal expandable frame having fixing pins for engagement with an aortic wall without aneurysmal expansion and proximal to renal arteries;

two iliac segments, each comprising a tubular body made of biocompatible fabric material attached to and supported by stents, each of said two iliac segments having a proximal end that can be connected to provide fluid communication between each tubular body of the two iliac segments and a respective one of the two tubular legs of the aortic bifurcation segment;

wherein a fixation part of the aortic bifurcation segment, distal with respect to the metal expandable frame, is configured for placement in a proximal neck of the abdominal aortic aneurysm, said fixation part being without biocompatible fabric material and comprising multidirectional fixing pins projecting from an outer surface of said fixation part for engagement with the aortic wall;

wherein the system comprises an additional inner segment that comprises a tubular body made of biocompatible fabric material and stents attached to the biocompatible fabric material, said additional inner segment being configured for fitting inside the fixation part along a length of the main tubular body and supporting it.

2. The system according to claim 1, further comprising an outer segment comprising a body made of biocompatible fabric material, wherein the outer segment is configured for placement around a part of the abdominal aorta distal to the renal arteries and configured to ensure tight pressing of the proximal neck of the abdominal aortic aneurysm to the proximal end of the aortic bifurcation segment.

3. The system according to claim 2, wherein the outer segment is a belt or ribbon 10 to 30 mm wide forming a circle and equipped with a fastener or buckle or threads for tying a knot.

4. The system according to claim 1, wherein the main tubular body, extending from the fixation part to the distal end that branches into the two tubular legs, comprises biocompatible fabric material supported by stents, said main tubular body forming a cylindrical structure.

5. The system according to claim 4, further comprising an outer segment comprising a body made of biocompatible fabric material, wherein the outer segment is configured for placement around a part of the abdominal aorta distal to the renal arteries and configured to ensure tight pressing of the proximal neck of the abdominal aortic aneurysm to the proximal end of the aortic bifurcation segment.

6. The system according to claim 5, wherein the outer segment is a belt or ribbon 10 to 30 mm wide forming a circle and equipped with a fastener or buckle or threads for tying a knot.

7. The system according to claim 1, wherein the main tubular body, being in fluid communication with the two tubular legs at the distal end thereof, is configured for additional fluid communication, at the proximal end thereof adjacent the fixation part, only with fluid contained within the aortic wall.

8. The system according to claim 7, further comprising an outer segment comprising a body made of biocompatible fabric material, wherein the outer segment is configured for placement around a part of the abdominal aorta distal to the renal arteries and configured to ensure tight pressing of the proximal neck of the abdominal aortic aneurysm to the proximal end of the aortic bifurcation segment.

9. The system according to claim 8, wherein the outer segment is a belt or ribbon 10 to 30 mm wide forming a circle and equipped with a fastener or buckle or threads for tying a knot.

10. The system according to claim 1, wherein the multidirectional fixing pins projecting from the outer surface of the fixation part are configured to simulate a plurality of circular suture rows.

11. The system according to claim 10, further comprising an outer segment comprising a body made of biocompatible fabric material, wherein the outer segment is configured for placement around a part of the abdominal aorta distal to the renal arteries and configured to ensure tight pressing of the proximal neck of the abdominal aortic aneurysm to the proximal end of the aortic bifurcation segment.

12. The system according to claim 11, wherein the outer segment is a belt or ribbon 10 to 30 mm wide forming a circle and equipped with a fastener or buckle or threads for tying a knot.

13. A method for treating the abdominal aortic aneurysm using a bifurcated stent graft system according to claim 1, comprising the steps of:
    introducing the aortic bifurcation segment into the abdominal aorta;
    placing the aortic bifurcation segment in contact with the tissues of the aorta so that the metal frame located at its proximal end is interlocked with the aortic wall proximal to the renal arteries, and part of the aortic bifurcation segment placed in the proximal neck of the abdominal aortic aneurysm is interlocked with the wall of the proximal neck of the abdominal aortic aneurysm;
    introducing the first iliac segment into the left or right iliac artery;
    placing the first iliac segment in contact with the tissues of the left or right iliac artery, respectively, and connecting the proximal end of the specified iliac segment with the lumen of one of the legs of the aortic bifurcation segment;
    introducing the second iliac segment into the other right or left iliac artery;
    placing the second iliac segment in contact with the tissues of the other right or left iliac artery, respectively, and connecting the proximal end of the specified iliac segment with the lumen of the other leg of the aortic bifurcation segment;
    introducing a balloon catheter and performing additional balloon dilatation of a part of the aortic bifurcation segment placed in the proximal neck of the abdominal aortic aneurysm;
    introducing an additional internal segment into the aortic-bifurcation segment;
    placing an additional inner segment in close contact with the part of the aortic bifurcation segment located in the proximal neck of the abdominal aortic aneurysm.

14. The method of treatment according to claim 13, further comprising, prior to the introduction of an additional internal segment,
    inserting a catheter is inserted into the aneurysmal sac through the stent cell of the part of the aortic bifurcation segment located in the proximal neck of the abdominal aortic aneurysm,
    thereafter filling the aneurysmal sac with a thrombotic substance or coils for embolization through the catheter, and
    removing the catheter.

15. A method of treatment according to claim 14, further comprising, after the installation of an additional inner segment,
    introducing, through laparoscopic or open surgical access around the abdominal aorta, an additional external segment below the renal artery branching, containing a body made of biocompatible fabric material, tightened until the walls of the proximal neck of the abdominal aortic aneurysm are tightly pressed against the part of the aortic bifurcation segment located in the proximal neck of the abdominal aortic aneurysm, and fixed on it, while the fixing multidirectional pins on the part of the aortic bifurcation segment located in the proximal neck of the abdominal aortic aneurysm pierce the biocompatible fabric material of the additional outer segment.

16. A method of treatment according to claim 13, further comprising, after the installation of an additional inner segment, introducing, through laparoscopic or open surgical access around the abdominal aorta, an additional external segment below the renal artery branching, containing a body made of biocompatible fabric material, tightened until the walls of the proximal neck of the abdominal aortic aneurysm are tightly pressed against the part of the aortic bifurcation segment located in the proximal neck of the abdominal aortic aneurysm, and fixed on it, while the fixing multidirectional pins on the part of the aortic bifurcation segment located in the proximal neck of the abdominal aortic aneurysm pierce the biocompatible fabric material of the additional outer segment.

\* \* \* \* \*